United States Patent [19]

Grzenia

[11] 4,094,309
[45] June 13, 1978

[54] MEDICAL ELECTRODE

[76] Inventor: Robert M. Grzenia, 9717 S. Homan Ave., Evergreen, Ill. 60642

[21] Appl. No.: 774,858

[22] Filed: Mar. 7, 1977

[51] Int. Cl.² .............................................. A61B 5/04
[52] U.S. Cl. ............................ 128/2.06 E; 128/2.1 E; 128/418; 128/DIG. 4; 174/133 R; 267/156
[58] Field of Search ........ 128/2.06 E, 2.1 E, 379–382, 128/384, 404, 410, 411, 416, 418, DIG. 4; 174/55 B; 267/156; 361/220, 223; 174/133 R

[56] References Cited

U.S. PATENT DOCUMENTS

| 415,274 | 11/1889 | Kane | 128/381 |
|---|---|---|---|
| 1,662,446 | 3/1928 | Wappler | 128/416 |
| 1,977,458 | 10/1934 | Stargardter | 267/156 |
| 2,956,795 | 10/1960 | Foster | 267/156 |
| 3,323,516 | 6/1967 | Salter | 128/2.06 E |
| 3,542,010 | 10/1970 | Love | 128/2.1 E |
| 3,545,430 | 12/1970 | Figar | 128/2.1 E |
| 3,599,629 | 8/1971 | Gordy | 128/2.06 E |
| 3,890,977 | 6/1975 | Wilson | 128/418 |
| 3,995,623 | 12/1976 | Blake | 128/2.06 E |

FOREIGN PATENT DOCUMENTS 6,714,179   4/1969   Netherlands ..................... 128/418

OTHER PUBLICATIONS

Nye, "A New EKG Electrode", The Lancet, Mar. 10, 1962, pp. 516-517.

Primary Examiner—Robert W. Michell
Assistant Examiner—Lee S. Cohen

[57] ABSTRACT

A medical electrode for taking an EKG or the like made of a bi-stable conductive spring material in the form of an elongated flat member which can assume a stable linear state and can be easily applied and attached to a patient's arm or leg by lightly striking it against the arm or leg is disclosed. Upon striking, the elongated member springs to its other stable stage, coiling around the arm and leg and making contact therewith. An electrical connector such as a contact gripping slit or snap fastener (or both), are provided on the member for connecting the electrode to a conventional EKG or like leads.

10 Claims, 8 Drawing Figures

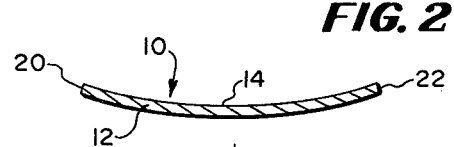
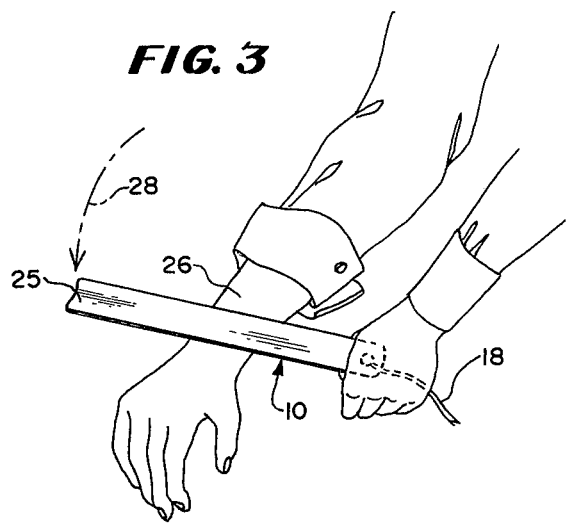
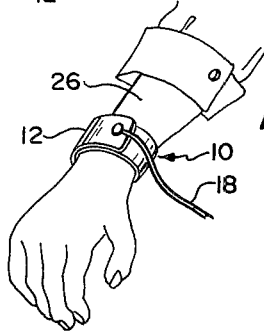
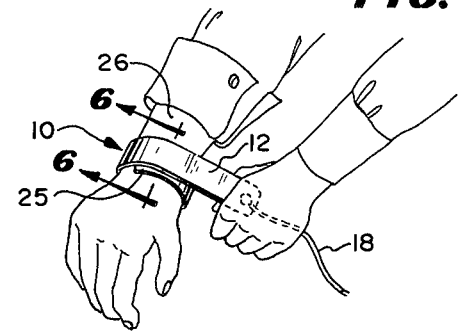
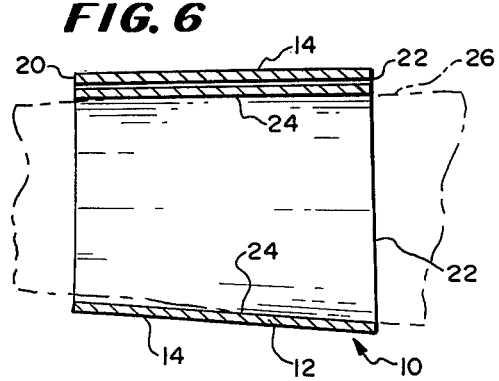
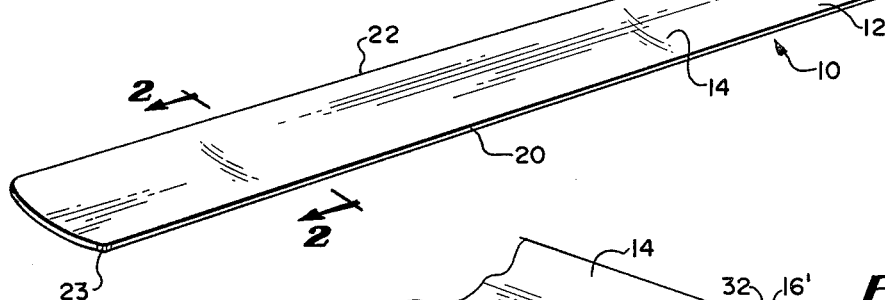
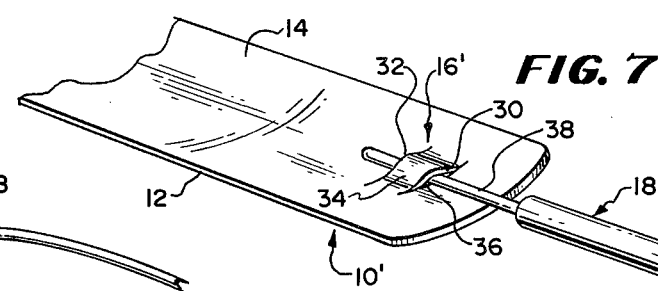
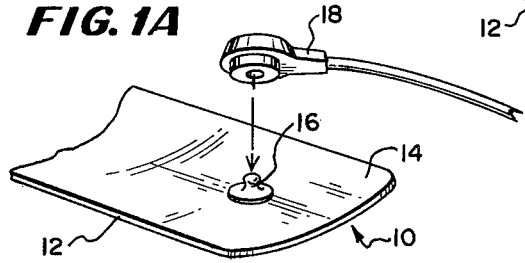

MEDICAL ELECTRODE

FIELD OF THE INVENTION

The present invention relates to medical electrodes and is especially concerned with a novel, useful and unobvious reusable electrode for attaching to the limb of a patient undergoing an EKG or like examination.

BACKGROUND OF THE INVENTION

Electrocardiograms (EKG) are a common medical diagnostic aid and are routinely taken in hospitals, clinics, doctors' offices, and, in emergency situations, anywhere. Such EKG examinations employ electrodes which are attached to the patient's skin at various places including, commonly, two or more limbs.

Many structures and means for attaching have been suggested in the past for such electrodes. Basically, these are of the disposable type, e.g., bandages or adhesives, or of the reusable type, e.g., suction cup electrodes or strap binding electrodes which use a belt buckle fastener (or more modern one use Velcro fasteners).

Among structures those suggested for the reusable type are described in U.S. Pat. No. 3,323,516 to Salter. The disposable electrodes often have the advantage of ease and speed of attachment since they are most commonly self-sticking, but since they are used only once, they are relatively expensive in the long run. The non-disposable electrodes have the advantage of being less expensive in the long run, but usually are relatively time consuming and difficult to apply. In emergency situations, where every second can count, this is a considerable drawback.

SUMMARY OF THE PRESENT INVENTION

A reusable electrode for use in medical examination, such as for an EKG or the like, for attachment to a patient's limb which combines the advantage of ease of application with the advantage of speedy application, constructed in accordance with the principles of the present invention comprises an elongated member having two stable states, one wherein it is generally linear and another wherein it is coiled upon itself. The elongated member is preferably made of conductive material such as stainless steel, but can be rendered conductive in other manners such as by coating. The member is provided with means (such as a snap fastener or slits or the like) at one end for attaching an electrical lead and is so constructed as to normally assume in its second or coiled shape a size smaller than the limb and is long enough to at least substantially encircle the limb.

The electrode of the present invention is easily attached as it need be only extended in its first or linear stable state, be held transverse to the limb, and have its side tapped (at about the middle of the side which is the inside when in the coiled state) against the patient's limb. The electrode then automatically springs into its second or coiled stable state encircling and contacting the limb. There are no clumsy straps to wrap around, tighten and fasten as the inventive electrode wraps itself around the limb and tightens itself against the patient's skin.

The inventive electrode is simple in construction, easy to manufacture and use, has no parts that move relative to one another to wear out or be replaced, and can be easily cleaned.

Other advantages and features of the present invention may best be understood by reference to the following description taken in connection with the accompanying drawings, in the several figures of which like reference numerals identify like elements.

BRIEF DESCRIPTION OF THE DRAWINGS

FIG. 1 is a perspective view of a medical electrode constructed in accordance in one stable state with the present invention together with an EKG lead.

FIG. 1A is a detail perspective view illustrating attachment of the EKG lead to the electrode of FIG. 1.

FIG. 2 is a cross sectional view of the electrode of FIG. 1, as seen from the line 2—2 in FIG. 1.

FIG. 3 is a perspective view of the electrode of FIGS. 1 and 2 with its attached EKG lead in use and about to be attached to a patient's arm.

FIG. 4 is a view similar to that of FIG. 3 showing the electrode partly in its second or coiled stable state just after contact with the patient's arm.

FIG. 5 is a third view similar to that of FIGS. 3 and 4 showing the electrode in its second or coiled stable state about the arm of the patient as it is used for taking an EKG.

FIG. 6 is a sectional view of the coiled electrode of FIGS. 1-5 as seen from lines 6—6 in FIG. 4 with the arm shown in phantom lines.

FIG. 7 is a partial detail perspective view of a modified construction for the electrode.

DETAILED DESCRIPTION

Referring to FIG. 1, there is depicted an electrode constructed in accordance with the principles of the present invention and generally designated by the number 10. The electrode includes an elongated member 12 with an outer surface 14. At one end of the elongated member 12 is provided means, in the form of a snap fastener 16, for attaching an electrical lead 18. As better seen in FIG. 1A, the lead 18 is press fitted over the fastener 16 and is reliably held thereby. Such a snap fastener means for attaching EKG leads to electrodes is in itself, of course, a conventional approach and is commonly used in disposable electrodes.

In overall shape the member 12 is generally rectangular with paralleled sides 20, 22 and rounded corners, such as the corner 23. The member 12 is, in its linear stable shape of FIG. 1, transversely curved, as best seen in FIG. 2, with its outer surface 14 being concave and its inner surface 24 being convex.

The member 14 is preferably made of spring metal and made such as is generally described in U.S. Pat. Nos. 2,609,191 or 2,956,795. Thus, the member 14 has two stable states: one, as shown in FIG. 1, its linear state, and another state wherein it is coiled upon itself. The least potential energy state is its coiled state and it tends to revert to that state from the linear state whenever the transverse curving (FIG. 2) is eliminated at any point along its length.

Referring to FIG. 3, one way of affixing the elctrode 10 about a limb is there illustrated. The medic or other person setting up the EKG simply takes the electrode in its linear state and holding it by the EKG lead connects and orients it across the limb, and strikes its inner surface, at about its middle length, lightly against a patient's limb, such as the arm 26, by moving the electrode 10 in the direction of the arrow 28.

The immediate effect of the striking is to cause the transverse curve to straighten at the point of contact and member 12 begins to coil. The coiling propagates from the point of impact to the free end 25. The free end 25 of the member 12 coils around the arm as shown in FIG. 4. Releasing the other end of the electrode 12 causes that end to also coil about the arm 26 as shown in FIG. 5. The electrode is now ready to use. The entire process from FIG. 3 to FIG. 5 can take a very short time, usually less than one second.

As can be seen in FIG. 6, the cross section of the member 12 is now flat and its inner surface 24 makes contact with the skin of the patient over a large surface. The natural tendency of the spring coil to close urges the surface 24 into close contact with the skin, but still accomodates itself to the shape of the limb. Note in FIG. 6 that the arm 26 is thicker at the edge 22 than at the edge 20. It also accomodates the out-of-round shape of the arm's cross section.

In FIG. 7 an alternative embodiment electrode 10′ wherein an alternative EKG lead receiving means 16′ is depicted for receiving a pin EKG lead 18′. In this case there are provided a pair of short parallel slits 30, 32 whose internal strip 34 is permanently raised above surface 14 to make a pair of apertures or openings, such as 36, to receive a pin 38 and hold it in tight contact against the surface 14 and the inner surface under strip 34. The aperture 36 is preferably sized such as to have the strip 34 be slightly displaced by the entry of the pin 38 and to captivate it in place by spring pressure. Upon assumption of the second or coiled shape, it should be noted, that the spring pressure on the pin 38 will be greatly increased so as to hold it more tightly during use. The electrode can be provided with the means 16 or 16′ or both could be placed on one end of the member 12 to allow it to be adapted to either pin or snap fastener EKG leads.

The member 12 is preferably made entirely of stainless steel, but can also be made of any other spring material, provided provision is made for proper electrical properties. If ordinary steel were used, a silver coating could be employed, at least on the inner surface 24. If a non-conductive spring is used, provision for electrical conduction such as coating with a conductor, must be made. It is desirable that the entire surface in contact with the skin be made conductive, but at least a major portion thereof should be. And, of course, that surface must be in electrical contact with the means 16 or 16′. The snap fastener 16 is preferably attached by means of a snap fastener female member 16F (FIG. 1) through a hole in the member 12 and the strip of means 16′ may be formed by punch press operation.

The coiled diameter of the member 12 should be smaller than the normally expected smallest patient's limb on which it is intended to be used and its length should be long enough to at least substantially, but preferably to completely encircle the limb. It may be convenient to provide longer units for use about legs, but it is possible in many cases to use the same electrode 10 for both limbs.

The preferred ranges are, for adults and larger children, a length of 12 inches to 14 inches, a width of ¾ inches to 1 ½ inches, preferably approximately one inch, and a coiled diameter of one inch to two inches, preferably one and one-half inches. For pediatric use, a ½ inch wide member 12 of about 6 inches length and a coiled size of approximately one inch is preferred.

Several prototypes of the invention have been built and tested successfully in their environment of use. One of these used a spring steel member 12 of approximately one inch across and fourteen inches in length which, when coiled, was approximately one and one-half inches in diameter. This size was found to be convenient for arm use.

It should now be appreciated that a new and unobvious electrode has been described in certain particular embodiments. It will be obvious to those skilled in this art that changes and modifications may be made without departing from the invention in its broader aspects and, therefor, the aim in the appended claims is to cover all such changes and modifications as fall within the invention's contribution to this art.

I claim:

1. A medical electrode for contacting the limb of a patient comprising a bi-stable spring elongated generally flat member having an outer surface and an inner surface and having two stable states, one in which it is generally linear and the other in which it is coiled about itself, with its inner surface facing inward, such member having a natural coiled state of a size smaller than the limb and being of such a length as to substantially encircle the limb, and means for attaching an electrical lead to the member, said member being constructed such that an electrically conductive path exists from at least a portion of the inner surface of said member to and through said electric lead attaching means to any electrical lead attached thereto, and said member having the property of naturally assuming the coiled state from the linear state in response to slight change in its shape.

2. The invention of claim 1 wherein said member is made of a conductive material which defines the electrically conductive path.

3. The invention of claim 1 wherein the attaching means is mounted at one end of said member.

4. The invention of claim 3 wherein said lead attaching means is a snap fastener.

5. The invention of claim 3 wherein said lead attaching means is a pin receiving and captivating aperture.

6. The invention of claim 5 wherein said pin receiving and captivating aperture is formed by a pair of slits in said member and a displaced strip therebetween.

7. The invention of claim 1 for use on a child wherein said member is approximately 6 inches in length and assumes a coiled state of approximately 1 inch in diameter.

8. The invention of claim 7 wherein said member is of stainless steel.

9. The invention of claim 1 for non-pediatric use wherein said member is 12 to 14 inches in length and coils to a diameter of approximately 1 ½ inches.

10. The method of using a medical electrode for contacting the limb of a patient to attach it to a patient's limb, said electrode comprising a bi-stable spring elongated generally flat member having an outer surface and an inner surface and having two stable states, one in which it is generally linear and the other in which it is coiled about itself, with its inner surface facing inward, such member having a natural coiled state of a size smaller than the limb and being such a length as to substantially encircle the limb, and means for attaching an electrical lead to the member, said member being constructed such that an electrically conductive path exists from at least a portion of the inner surface of said member to and through said electric lead attaching means to any electrical lead attached thereto, and said member having the property of naturally assuming the coiled state from the linear state in response to slight change in its shape, said method comprising the steps of providing the electrode in its linear state and while securing one end and leaving its other end free, striking its inner surface amid its length against the limb, while orienting the longitudinal member transversely to the limb, whereby the members free end is caused to coil about the limb and thereafter releasing the secured end so that it may coil about the limb also.

* * * * *